United States Patent [19]

Thomaides et al.

[11] Patent Number: 5,626,840
[45] Date of Patent: May 6, 1997

[54] USE OF POLYURETHANES WITH CARBOXYLATE FUNCTIONALITY FOR HAIR FIXATIVE APPLICATIONS

[75] Inventors: John Thomaides, Berkeley Heights; Julie V. Russo, Freehold; Gary T. Martino, Plainsboro; Dilip K. Ray-Chaudhuri, Bridgewater, all of N.J.

[73] Assignee: National Starch and Chemical Investment Holding Corporation, Wilmington, Del.

[21] Appl. No.: 565,353

[22] Filed: Nov. 30, 1995

Related U.S. Application Data

[63] Continuation-in-part of Ser. No. 351,903, Dec. 8, 1994, abandoned, which is a continuation-in-part of Ser. No. 43,241, Apr. 6, 1993, abandoned.

[51] Int. Cl.$^6$ ........................................................ A61K 7/11

[52] U.S. Cl. .................. 424/70.11; 424/101; 424/DIG. 2
[58] Field of Search ............................... 426/70.1, 70.11, 426/DIG. 2

[56] References Cited

U.S. PATENT DOCUMENTS 3,412,054  11/1968  Milligan et al. ........................... 260/18

FOREIGN PATENT DOCUMENTS 47-46332  6/1970  Japan .

*Primary Examiner*—Jyothsna Venkat
*Attorney, Agent, or Firm*—Jane E. Gennaro

[57] ABSTRACT

A polyurethane, soluble or dispersible in water, prepared from an organic diisocyante, a diol, and a 2,2-hydroxymethyl-substituted carboxylic acid is neutralized with a cosmetically acceptable organic or inorganic base and formulated into a hair fixative composition containing low amounts of volatile organic solvent.

12 Claims, No Drawings

USE OF POLYURETHANES WITH CARBOXYLATE FUNCTIONALITY FOR HAIR FIXATIVE APPLICATIONS

This is a continuation in part of Ser. No. 08/351,903, filed 8 Dec. 1994 now abandoned, which is a continuation in part of Ser. No. 08/043,241 filed 6 Apr. 1993, now abandoned.

FIELD OF THE INVENTION

This invention pertains to hair fixative compositions that are prepared with polyurethanes containing pendant free carboxyl groups neutralized with standard cosmetically acceptable bases.

BACKGROUND OF THE INVENTION

Most hair fixative compositions contain a film-forming polymer, which acts as the fixative, and a delivery system, which is usually an alcohol or a mixture of alcohol and water. In the case of aerosol delivery, the delivery system will also contain a propellant, which is typically a volatile hydrocarbon. Due to environmental regulations controlling the emission of volatile organic compounds (VOCs) into the atmosphere, these alcohol and hydrocarbon delivery systems are becoming less acceptable, and it is foreseen that water will become a greater component in hair fixative compositions. Hair fixative polymers taught for use in aqueous based systems are known, for example, those disclosed in Japanese publication JP 47-46332. However, many of these exhibit a loss of performance properties in aqueous systems, for example, curl retention and on-hair stiffness are inferior, and in other cases the solution viscosity increases, and if delivered by aerosol, the composition foams at the valve actuator and on the hair. These factors have prompted the search for good performing hair fixative polymers that are soluble or dispersible in aqueous or in low VOC systems, that is, systems containing 80% or less VOCs.

SUMMARY OF THE INVENTION

This invention is a hair fixative composition comprising a water soluble or dispersible polyurethane that, despite its solubility or dispersibility in water, also demonstrates good humidity resistance, good spray characteristics, and forms a clear, transparent, glossy film that is easily removable with water (its rinsability) or with water and shampoo.

The hair fixative composition comprises (A) an effective amount of the polyurethane to perform as a hair fixative in an all water or in an alcohol-water solvent system; (B) an effective amount of a cosmetically acceptable organic or inorganic base to neutralize a sufficient proportion of the available carboxyl groups on the polyurethane to make the polyurethane soluble or dispersible in water or in a mixture of water and a polar organic solvent; and (C) a solvent comprising (i) water, and (ii) 0–90% by weight of a polar organic solvent, based on the weight of the solvent.

The polyurethane is a fully reacted carboxylated linear polyurethane prepared as the reaction product of (i) one or more 2,2-hydroxymethyl-substituted carboxylic acids present in an amount to give 0.35–2.25 milliequivalents of carboxyl functionality per gram of polyurethane, (ii) 10–90% by weight, based on the weight of the polyurethane, of one or more organic compounds, other than the 2,2-hydroxymethyl-substituted carboxylic acids, each having no more than two active hydrogen atoms, and a number average molecular weight of greater than 1000, and (iii) one or more organic diisocyanates present in a sufficient amount to react with the active hydrogens of the 2,2-hydroxymethyl-substituted carboxylic acids and the organic compounds, excepting the hydrogen on the carboxylate of the 2,2-hydroxymethyl-substituted carboxylic acid.

In aerosol systems, the hair fixative composition will further comprise up to 60% by weight of a propellant based on the weight of the total hair fixative composition.

DETAILED DESCRIPTION OF THE INVENTION

The polyurethanes suitable for use in hair fixative formulations according to this invention are fully reacted carboxylated linear polymers. These polyurethanes are used in an effective amount to achieve hair holding and humidity resistance properties. They are preferably present in amounts from 1–20% by weight of the hair fixative composition, and more preferably in amounts from 1–10% by weight.

The incorporation of the 2,2-hydroxymethyl-substituted carboxylic acid introduces pendant carboxylic acid groups into the polymer chain, which after neutralization render the polyurethane soluble or dispersible in water or in mixtures of water with other polar solvents. Using these polyurethanes as the active ingredient, hair fixative formulations can be made that have a high solids content with low viscosity. A high solids content supplies an effective amount of polymer to the hair in a minimum amount of solvent to obtain good holding power. Low viscosity permits effective atomization at the spray nozzle. Thus, a hair fixative product suitable for use in either aerosol or nonaerosol formulations can be achieved. The use of 2,2-hydroxymethyl-substituted carboxylic acids also imparts increased film hardness and rigidity to the polyurethane, properties that are desirable for hair fixatives.

The 2,2-hydroxymethyl-substituted carboxylic acids are represented by the formula

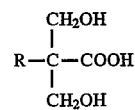

in which R represents hydrogen, or $C_1$–$C_{20}$ alkyl, preferably $C_1$–$C_8$ alkyl. Specific examples include 2,2-di(hydroxymethyl)acetic acid, 2,2-di(hydroxymethyl)propionic acid, 2,2-di-(hydroxymethyl)butyric acid, 2,2-di(hydroxymethyl)pentanoic acid, and the like. The preferred acid is 2,2-di-(hydroxymethyl)propionic acid. The 2,2-hydroxymethyl-substituted carboxylic acids are present in an amount to give 0.35–2.25, preferably 0.5–1.85, milliequivalents of carboxyl functionality per gram of polyurethane, and in general this is about 5–30% by weight of the polyurethane polymer.

The organic compounds that are active with isocyanate and that may be used for the preparation of the polyurethane polymers of this invention have no more than two active hydrogen atoms (as determined by the Zerewitinoff method). The active hydrogen atoms are usually attached to oxygen, nitrogen or sulfur atoms. The organic compounds will be present in an amount of 10–90% by weight of the polyurethane, preferably in an amount of 15–70% by weight. Preferably, the total or major portion of any compound used will have a number average molecular weight of 1000 or greater up to about 20,000. Optionally, it is possible to use compounds with a molecular weight lower than 1000 in a minor proportion, provided that the solubility or dispersibility of the resultant polymer in water is not affected. Preferably, these compounds will be linear so that gelling during polymerization is prevented, but small amounts of non-linear compounds may be used provided their use does not cause gelling.

The preferred organic compounds with two active hydrogen atoms are the linear difunctional polyethylene and polypropylene glycols, especially those that are available commercially and produced by the reaction of ethylene (or propylene) oxide with water, ethylene (or propylene) glycol, or diethylene (or dipropylene) glycol in the presence of sodium hydroxide as a catalyst. These polyglycols have number average molecular weights preferably of greater than 1,000 to about 8,000. Polyglycols that are homogeneous in molecular weight, or a mixture of glycols that differ in molecular weight can be used. It is also possible to copolymerize small amounts of additional alkylene oxides into the polyglycol.

Other suitable organic compounds with two active hydrogen atoms are those having hydroxyl, carboxyl, amino or mercapto groups. Among these, the preferred are polyhydroxy compounds, such as, polyether diols, polyester diols, polyacetal diols, polyamide diols, poly(ester amide) diols, poly(alkylene ether)diols, polythioether diols, and polycarbonate diols. Compounds that contain two or more different groups within these classes may also be used, for example, amino alcohols and amino alcohols containing two amino groups and one hydroxyl group. It is preferred to use difunctional compounds although small amounts of tri- (and greater) functional compounds may be used.

Suitable polyether diols are, for example, the condensation products of ethylene oxide, propylene oxide, butylene oxide, or tetrahydrofuran, and their copolymerization, graft or block polymerization products, such as, mixed ethylene oxide, propylene oxide condensates, and the graft polymerization products of the reaction of olefins under high pressure with the mentioned alkylene oxide condensates. Suitable polyethers are prepared by the condensation of the mentioned alkylene oxides with polyhydric alcohols, such as, ethylene glycol, 1,2-propylene glycol and 1,4-butanediol.

Suitable polyester diols, poly(ester amide) diols, and polyamide diols are preferably saturated, and are obtained, for example, from the reaction of saturated or unsaturated polycarboxylic acids with saturated or unsaturated polyhydric alcohols, diamines, or polyamines. Suitable carboxylic acids for preparing these compounds include, for example, adipic acid, succinic acid, phthalic acid, terephthalic acid, and maleic acid. Suitable polyhydric alcohols for preparing the polyesters include, for example, ethylene glycol, 1,2-propylene glycol, 1,4-butanediol, neopentyl glycol, and hexanediol. Amino alcohols, for example, ethanolamine, are also useful. Suitable diamines for preparing the poly(ester amide) diols and polyamide diols are, for example, ethylene diamine and hexamethylene diamine.

Suitable polyacetals can be prepared, for example, from 1,4-butanediol or hexanediol and formaldehyde. Suitable polythioethers can be prepared, for example, as the condensation products of thiodiglycol either alone or in combination with other glycols, such as, ethylene glycol, 1,2-propylene glycol or with other polyhydroxy compounds as disclosed above. Polyhydroxy compounds that already contain urea or urethane groups, and natural polyols, which may be further modified, for example, castor oil and carbohydrates, may also be used.

In preparing the polyurethane polymer, in addition to the organic compound having no more than two active hydrogen atoms, which in many cases is a high molecular weight compound, it may be desirable to chain extend the polymer using an organic compound with a lower molecular weight, preferably less than about 300 and more than 60. Typical chain extending agents include saturated or unsaturated glycols, such as, ethylene glycol, diethylene glycol, triethylene glycol and the like; amino alcohols, such as, ethanolamine, propanolamine, butanolamine, and the like; mono- and dialkoxylated aliphatic, cycloaliphatic, aromatic and heterocyclic primary amines, such as, N-methyldiethanolamine, N-oleyl diethanolamine, N-cyclohexyl diisopropanolamine, N,N-dihydroxyethyl-p-toluidine, N,N-dihydroxy-propylnaphthylamine and the like; diamines, such as ethylene diamine, piperazine, N-N-bis-gamma-aminopropyl-N-methyl-amine and the like; carboxylic acids including aliphatic, cycloaliphatic, aromatic and heterocyclic dicarboxylic acids, such as, oxalic acid, malonic acid, succinic acid, glutaric acid, adipic acid, sebacic acid, terephthalic acid, 1,5-dicarboxylic naphthalic acid, maleic acid, fumaric acid, diglycolic acid, quinolinic acid, lutidinic acid and the like; amino carboxylic acids, such as, glycine, alpha and beta-alanine, 6-aminocaproic acid, 4-aminobutyric acid, p-aminobenzoic acid, 5-aminonaphthoic acid and the like. The preferred chain extending agents are aliphatic diols.

The organic polyisocyanates or mixtures of polyisocyanates that are reacted with the organic compound are aliphatic or aromatic polyisocyanates, or mixtures of those. The polyisocyanates are preferably diisocyanates in order to result in a linear polymer, although minor amounts of trifunctional isocyanates may be used in conjunction with the diisocyanates. The isocyanate will be present in a sufficient amount to react with the active hydrogens of the 2,2-hydroxymethyl-substituted carboxylic acid and the organic compounds, excepting the hydrogen on the carboxylate of the 2,2-hydroxymethyl-substituted carboxylic acid. This amount will vary depending on the amounts of the carboxylic acid and organic compounds.

Exemplary diisocyanates include, but are not limited to, methylene di-p-phenyl diisocyanate, methylene-bis(4-cyclohexylisocyanate), isophorone diisocyanate, toluene diisocyanate, 1,5-naphthalene diisocyanate, 4,4'-diphenylmethane diisocyanate, 2,2'-dimethyl-4,4'-diphenylmethane diisocyanate, 4,4'-dibenzyldiisocyanate, 1,3-phenylene diisocyanate, 1,4-phenylene diisocyanate, mixtures of 2,4- and 2,6-toluene diisocyanate, 2,2'-dichloro-4,4'-diisocyanato diphenylmethane, 2,4-dibromo-1,5-diisocyanato naphthalene, butane-1,4-diisocyanate, hexane-1,6-diisocyanate, cyclohexane-1,4-diisocyanate, bis(1-isocyanato-1-methylethyl)-benzene, and trimethylhexamethylenediisocyanate.

If it is desired not to chain extend the polymer, the reaction of the diisocyanate with the organic compound having two active hydrogen atoms is quenched by the addition of a monofunctional active hydrogen-containing compound to consume any residual isocyanate functionality. Examples of these quenching compounds are well known in the art; for these systems, the preferred quenching compound is ethanol.

The urethane polymerization is carried out in the reaction medium with or without typical urethane reaction catalysts known in the art. Suitable catalysts include dibutyl tin dilaurate; the stannous salts of carboxylic acids having from 2 to 18 carbon atoms, such as, stannous laurate, stannous stearate, stannous acetate, stannous butyrate, stannous octoate and the like, and mixtures of those. Other suitable catalysts include dibutyl tin oxide, dibutyl tin sulfide, lead resinate, lead benzoate, lead salicylate, lead 2-ethyl hexoate, lead oleate, iron acetyl acetonate, cobalt benzoate, tetra(2-ethyl hexyl)titanate, tetra butyl titanate, and the like. Many other compounds accelerate the reaction of a hydroxyl or other groups with an isocyanate in preference to certain other reactions of the isocyanate group, and any of these compounds may be used. Those skilled in the art will choose a specific catalyst to confer desired characteristics to individual urethane reactions. The preceding specific compounds are the preferred compounds and are given for the purpose of illustration and not limitation. In addition, any suitable tertiary amine may be used alone or with the metallic catalyst, for example, triethylene diamine, N-ethyl morpholine, N-methyl morpholine, or 4-dimethyl amino ethyl piperazine.

With respect to the proportion of reactants, the reactants should be selected so that the molecular ratio of isocyanate groups to active hydrogen atoms is as close to 1:1 as is practicable. It is appreciated that this exact ratio may not always be attained in practice; therefore, a ratio between about 0.7:1 and 1.3:1, and preferably between about 0.9:1 and 1.2:1, should be sought, and any excess diisocyanate, as discussed previously, can be quenched with the monofunctional active hydrogen containing compound.

The polymerization is carried out according to known in the art polyurethane polymerization techniques. Exemplary polymerizations and reaction conditions are given in the examples. Other suitable procedures are described in D. Dietrich, *Progress in Organic Coatings*, 9, 281 (1981), "Aqueous Emulsions, Dispersions and Solutions of Polyurethanes: Synthesis and Properties," and in J. W. Rosthauser & K. Nachtkamp, *Adv. Urethane Science & Technology*, p 121 (1987), "Waterborne Polyurethanes".

The carboxylated polyurethanes are neutralized by the standard cosmetically acceptable bases known and used in the art, and these may be used singly or in combination. The preferred bevels of neutralization range from 50–90%, depending on the acidity of the polymer. The preferred bases are sodium hydroxide, potassium hydroxide, 2-amino-2-methyl-1-propanol, histidine, tris(hydroxymethyl) aminomethane, triethanolamine and triethylamine. The choice of the base and the degree of neutralization also affect the flexibility of the resultant hair fixative when sprayed on the hair, giving a soft or a hard hold. One or more of the bases may be used, and the choice of which base or bases to utilize and the degree of neutralization required to achieve flexibility is within the expertise of one skilled in the art. In general, however, the amount of base for neutralization will be within the range of 0.05–0.80% based on the total weight of the composition, although it will be recognized that individual formulations may require neutralization outside this range.

Neutralization renders the polymers soluble or dispersible in water for easy formulation into aqueous hair sprays (and thus contributes to removability). The neutralized polymers can be formulated solely in water as the solvent, or the solvent system can be a blend of polar organic solvent and water. Typically, the organic solvent will be an alcohol or ketone. Particularly suitable solvents are low boiling alcohols that are compatible with other components in the hair fixative composition, for example, $C_1$–$C_4$ straight or branched chain alcohols. Exemplary polar solvents are ethanol, propanol, isopropanol, butanol, acetone, dimethylether and dimethoxymethane.

Hair fixative compositions that are intended to be delivered in an aerosol system additionally will require a propellant. While any of the known propellants may be used in these compositions, preferred propellants include the hydrocarbons, particularly the lower boiling hydrocarbons such as $C_3$–$C_6$ straight and branched chain hydrocarbons, for example, propane, butane, isobutane and mixtures of those. Other preferred propellants include the ethers, such as dimethyl ether; hydrofluorocarbons, such as, 1,1-difluoroethane; and the compressed gases, such as nitrogen, air and carbon dioxide. The amount of propellant used in the hair fixative compositions of this invention may vary from about 0 to 60% by weight of the hair spray composition and preferably from about 0 to 40% by weight, based on the weight of the total composition.

An important consideration in determining the amount of organic solvent, or organic solvent and propellant, to be used in the hair fixative composition is the total amount of volatile organic compound (VOC) content, and any upper limit of VOC content that may be mandated by environmental regulations. While these compositions may have a wide range of VOC content, from 0 to 90% by weight, due to current environmental regulations it is preferred that there be less than about 80%, more preferred less than about 55%, and most preferred less than about 20% by weight VOC content, based on the weight of the composition. The balance of the hair fixative composition will be water and the neutralized polyurethane.

Optional conventional additives may also be incorporated into the hair fixing composition of this invention to provide certain modifying properties to the composition. Included among these additives are plasticizers, such as glycerine, glycol and phthalate esters; silicones; emollients, lubricants and penetrants, such as lanolin compounds; fragrances and perfumes; UV absorbers; dyes and other colorants; thickeners; anticorrosion agents; detackifying agents; combing aids; antistatic agents; preservatives; and foam stabilizers. These additives are present in small, effective amounts to accomplish their function, and generally will comprise from about 0.1 to 10% by weight each, and from about 0.1 to 20% by weight total, based on the weight of the composition.

The resulting hair fixing compositions exhibit all of the characteristics required of such a product in systems ranging from 0 to 90% VOC. The films found are clear, hard, glossy and provide humidity resistance while being readily removable.

EXAMPLES

Although solubility or dispersibility in a low VOC formulation is a necessary characteristic of a good low VOC hair spray resin, not all water soluble or dispersible resins are good hair spray resins. Indeed, it might be expected that solubility would adversely affect humidity resistance, which is a key performance requirement. The following examples disclose the preparation of polyurethanes containing varying levels of dimethylol propionic acid and the results of humidity resistance testing on hair fixative formulations prepared from those polyurethanes. The results show that the polyurethanes with the specified carboxylic acid content not only are suitable for formulation into low VOC hair sprays, but they also have very good on-hair performance according to the criteria generally used in the industry to evaluate hair spray resins.

Syntheses of Polyurethanes

Polyurethane A.

A polyurethane containing 16.7% by weight dimethylol propionic acid was prepared (total carboxylate functionality: 1.25 meq/g). The product was isolated as an emulsion in water.

Reagents:

| | | |
|---|---|---|
| 1a. | Polypropylene glycol (1000 molecular weight) | 34.12 g |
| 1b. | Polypropylene glycol (3000 molecular weight) | 47.36 g |
| 2. | Polyethylene glycol (8000 molecular weight) | 10.00 g |
| 3. | Acetone (anhydrous) | 200.0 g |
| 4. | Methylenedi-p-phenyl diisocyanate (260 effective MW) | 75.12 g |
| 5. | Dibutyl tin dilaurate | 0.20 g |
| 6. | Dimethylol propionic acid | 33.40 g |
| 7. | Ethanol | 5.0 g |
| 8. | 1.0 N Sodium Hydroxide | 100.0 mL |
| 9. | Deionized water | as needed to bring reagent 8 to 300 g |

A one liter four-neck round bottom flask equipped with three stoppers and a vacuum adapter was charged with reagents 1 and 2. The reaction mixture was heated to 110° C. under dynamic vacuum (<1 mm Hg) for 1 hour. The vacuum was released with nitrogen, and the flask was fit with a mechanical stirrer, thermometer, stopper, and a gas inlet-topped condenser. The reaction vessel was placed under a positive pressure of nitrogen and was maintained in this manner throughout the course of the urethane condensation reaction. The vessel was charged with reagent 3. The resulting mixture was brought to reflux and held there until a homogenous solution was obtained.

The reaction mixture was allowed to cool to less than 50° C. Reagents 4 and 5 were added, and the reaction was brought to reflux. The reaction was allowed to stir at reflux for 5 hours. Reagent 6 was added, and the reaction was stirred at reflux for an additional 11 hours. Reagent 7 was then added to the reaction mixture, and the reaction was allowed to stir at reflux for 1 hour.

Reagent 8 was charged into an addition funnel and then a sufficient quantity of reagent 9 was added to bring the total weight of reagent in the addition funnel to 300 g. The contents of the funnel were added to the reaction mixture uniformly over a 3 hour period at 60° C. When the addition was complete, the flask was equipped for simple distillation, and distillation of solvent from the reaction mixture was started. When the pot temperature reached 90° C., steam distillation of the reaction mixture via the introduction of sub-surface steam was commenced. The steam distillation was continued until the pot temperature reached 100° C. and was maintained at 100° C. for 1 hour. A stable, fully aqueous emulsion was obtained at the conclusion of the steam distillation. The yield was 524.3g (37.6% solids). The neutralization equivalent of the emulsion was 0.286 meq/g. This corresponds to a neutralization equivalent of 0.761 meq/g on a 100% solids basis.

Polyurethane B.

A polyurethane containing 14.6% by weight dimethylol propionic acid (total carboxylate functionality: 1.09 meq/g) and 2% by weight N-methyl diethanolamine was prepared. This polyurethane contains both cationic and anionic functionality. The product was isolated as an emulsion in water.

Reagents:

| | | |
|---|---|---|
| 1. | Polypropylene glycol (2000 molecular weight) | 51.30 g |
| 2. | Polyethylene glycol (8000 molecular weight) | 16.57 g |
| 3. | Dimethylol propionic acid | 21.95 g |
| 4. | 2-Butanone | 190.4 g |
| 5. | Methylenedi-p-phenyl diisocyanate (260 effective MW) | 57.23 g |
| 6. | Dibutyl tin dilaurate | 0.20 g |
| 7. | N-methyl diethanolamine | 3.09 g |
| 8. | Ethanol | 5.0 g |
| 9. | 1.0 N Sodium hydroxide | 75.0 mL |
| 10. | Deionized water | as needed to bring reagent 9 to 325 g |

A one liter four-neck round bottom flask was equipped with a mechanical stirrer, thermometer, stopper, and a Dean & Stark-type receiver with draw-off valve fit with a gas inlet-topped condenser. The reaction vessel was placed under a positive pressure of nitrogen and was maintained in this manner throughout the course of the urethane condensation reaction. The vessel was charged with reagents 1, 2, 3, and 4. The resulting suspension was brought to reflux, and a total of 39.9g 2-butanone was distilled from the reaction vessel via the Dean & Stark receiver.

The reaction mixture was allowed to cool to less than 40° C. Reagents 5 and 6 added, and the reaction temperature was brought to 60° C. The reaction was allowed to stir at 60° C. for 19 hours at which time the residual isocyanate was found to be 0.77% (theory: 0.81%). Reagent 7 was added at this time, and the reaction was stirred at 60° C. for an additional 1.5 hours. The residual isocyanate was re-measured and found to be 0.11% (theory: 0.07%). Reagent 8 was then added to the reaction mixture, and the reaction was allowed to stir at 60° C. for 1 hour.

Reagent 9 was charged into an addition funnel and then a sufficient quantity of reagent 10 was added to bring the total weight of reagent in the addition funnel to 325 g. The contents of the funnel were added to the reaction mixture uniformly over a 3 hour period at 60° C. When the addition was complete, simple distillation at atmospheric pressure of solvent from the reaction mixture was started. When the pot temperature reached 90° C., steam distillation of the reaction mixture via the introduction of sub-surface steam was commenced. The steam distillation was continued until the pot temperature reached 100° C. and was maintained at 100° C. for 1 hour. A stable, fully aqueous emulsion was obtained at the conclusion of the steam distillation. The yield was 495.8 g (28.6% solids). The neutralization equivalent of the emulsion was 0.167 meq/g. This corresponds to a neutralization equivalent of 0.584 meq/g on a 100% solids basis.

Polyurethane C.

A polyurethane containing 24.6% by weight dimethylol propionic acid was prepared (total carboxylate functionality: 1.83 meq/g). The product was isolated as an emulsion in water.

Reagents:

| | | |
|---|---|---|
| 1. | Polypropylene glycol (2000 molecular weight) | 21.47 g |
| 2. | Polyethylene glycol (8000 molecular weight) | 16.50 g |
| 3 | Dimethylol propionic acid | 36.31 g |
| 4. | 2-Butanone | 336.2 g |
| 5. | Methylenedi-p-phenyl diisocyanate (260 effective MW) | 75.83 g |
| 6. | Dibutyl tin dilaurate | 0.2 g |
| 7. | Ethanol | 5.0 g |
| 8. | 1.0 N Sodium Hydroxide | 100.0 mL |
| 9. | Deionized water | as needed to bring reagent 8 to 300 g |

A one liter four-neck round bottom flask was equipped with a mechanical stirrer, thermometer, stopper, and a Dean & Stark-type receiver with draw-off valve fit with a gas inlet-topped condenser. The reaction vessel was placed under a positive pressure of nitrogen and was maintained in this manner throughout the course of the urethane condensation reaction. The vessel was charged with reagents 1, 2, 3, and 4. The resulting suspension was brought to reflux, and a total of 43 g 2-butanone was distilled from the reaction vessel via the Dean & Stark receiver.

The reaction mixture was allowed to cool to less than 40° C. Reagents 5 and 6 were added, and the reaction temperature was brought to 60° C. The reaction was allowed to stir at 60° C. for 20 hours at which time the residual isocyanate was found to be 0.05% (theory: 0.15%). Reagent 7 was added at this time, and the reaction was stirred at 60° C. for an additional hour.

Reagent 8 was charged into an addition funnel and then a sufficient quantity of reagent 9 was added to bring the total weight of reagent in the addition funnel to 300 g. The contents of the funnel were added to the reaction mixture uniformly over a 3 hour period at 60° C. When the addition was complete, simple distillation at atmospheric pressure of solvent from the reaction mixture was started. When the pot temperature reached 90° C., steam distillation of the reaction mixture via the introduction of sub-surface steam was commenced. The steam distillation was continued until the pot temperature reached 100° C. and was maintained at 100° C. for 45 minutes. A stable, fully aqueous emulsion was obtained at the conclusion of the steam distillation. The yield was 401.3 g (34.1% solids). The neutralization equivalent of the emulsion was 0.286 meq/g. This corresponds to a neutralization equivalent of 0.839 meq/g on a 100% solids basis.

Polyurethane D.

A polyurethane containing 7.5% by weight dimethylol propionic acid was prepared (total carboxylate functionality: 0.56 meq/g). The product was isolated as an emulsion in water.

Reagents:

| 1. | Polypropylene glycol (2000 molecular weight) | 87.55 g |
|---|---|---|
| 2. | Polyethylene glycol (8000 molecular weight) | 16.48 g |
| 3. | Dimethylol propionic acid | 11.26 g |
| 4. | 2-Butanone | 190.7 g |
| 5. | Methylenedi-p-phenyl diisocyanate (260 effective MW) | 34.68 g |
| 6. | Dibutyl tin dilaurate | 0.2 g |
| 7. | Ethanol | 5.0 g |
| 8. | 0.94 N Sodium Hydroxide | 35.8 mL |
| 9. | Deionized water | as needed to bring reagent 8 to 275 g |

The emulsion was prepared following the procedure outlined for polyurethane C. The yield was 611 g (23.9% solids). The neutralization equivalent of the emulsion was 0.080 meq/g. This corresponds to a neutralization equivalent of 0.33 meq/g on a 100% solids basis.

Polyurethane E.

A polyurethane containing 14.6% by weight dimethyl propionic acid was prepared (total carboxylate functionality: 1.09 meq/g). A cycloaliphatic diisocyanate was used in the synthesis. The product was isolated as an emulsion in water.

Reagents:

| 1. | Polypropylene glycol (2000 molecular weight) | 63.48 g |
|---|---|---|
| 2. | Polyethylene glycol (8000 molecular weight) | 11.27 g |
| 3. | Dimethylol propionic acid | 22.03 g |
| 4. | 2-Butanone | 183.0 g |
| 5. | Methylene bis-(4-cyclohexyl isocyanate) (264 effective MW) | 53.90 g |
| 6. | Dibutyl tin dilaurate | 0.5 g |
| 7. | Ethanol | 10.0 g |
| 8. | 0.94 N Sodium Hydroxide | 34.6 mL |
| 9. | Deionized water | as needed to bring reagent 8 to 275 g |

A one liter four-neck round bottom flask was equipped with a mechanical stirrer, thermometer, stopper, and a Dean & Stark-type receiver with draw-off valve fit with a gas-inlet-topped condenser. The reaction vessel was placed under a positive pressure of nitrogen and was maintained in this manner throughout the course of the urethane condensation reaction. The vessel was charged with reagents 1, 2, 3, and 4. The resulting suspension was brought to reflux, and a total of 37.5 g 2-butanone was distilled from the reaction vessel via the Dean & Stark receiver.

The reaction mixture was allowed to cool to less than 60° C. Reagents 5 and 6 were added, and the reaction temperature was brought to 70°–75° C. The reaction was allowed to stir at 70°–75° C. for 30 hours at which time the residual isocyanate was found to be 0.26% (theory: 0.20%). Reagent 7 was added at this time, and the reaction was stirred at 70°–75° C. for an additional 10 hours.

Reagent 8 was charged into an addition funnel and then a sufficient quantity of reagent 9 was added to bring the total weight of reagent in the addition funnel to 275 g. The contents of the funnel were added to the reaction mixture uniformly over a 3 hour period at 60° C. When the addition was complete, simple distillation at atmospheric pressure of solvent from the reaction mixture was started. When the pot temperature reached 90° C., steam distillation of the reaction mixture via the introduction of sub-surface steam was commenced. The steam distillation was continued until the pot temperature reached 100° C. and was maintained at 100° C. for 30 minutes. A stable, fully aqueous emulsion was obtained at the conclusion of the steam distillation. The yield was 458.1 g (31.1% solids). The neutralization equivalent of the emulsion was 0.257 meq/g. This corresponds to a neutralization equivalent of 0.826 meq/g on a 100% solids basis.

Polyurethane F.

A polyurethane containing 16.7% by weight dimethylol propionic acid was prepared (total carboxylate functionality: 1.25 meq/g). The product was isolated as an emulsion in water.

Reagents:

| 1. | Polypropylene glycol (1000 molecular weight) | 30.99 g |
|---|---|---|
| 2. | Polyethylene glycol (3000 molecular weight) | 60.49 g |
| 3. | Acetone (anhydrous) | 200.0 g |
| 4. | Methylenedi-p-phenyl diisocyanate (260 effective MW) | 75.12 g |
| 5. | Dibutyl tin dilaurate | 0.20 g |
| 6. | Dimethylol propionic acid | 33.43 g |
| 7. | Ethanol | 5.0 g |

| 8. | 1.0 N. Sodium Hydroxide | 100.0 mL |
| 9. | Deionized water | as needed to bring reagent 8 to 300 g |

The emulsion was prepared following the procedure outlined in the synthesis of polyurethane A. The yield was 492.2 g (36.7% solids). The neutralization equivalent of the emulsion was 0.273 meq/g. This corresponds to a neutralization equivalent of 0.744 meq/g on a 100% solids basis.

Polyurethane G.

A polyurethane containing 5% by weight dimethylol propionic acid was prepared (total carboxylate functionality: 0.37 meq/g). The product was isolated as an emulsion in water.

Reagents:

| 1. | Polypropylene glycol (2000 molecular weight) | 97.82 g |
| 2. | Polyethylene glycol (8000 molecular weight) | 16.50 g |
| 3. | Dimethylol propionic acid | 7.50 g |
| 4. | 2-Butanone | 193.7 g |
| 5. | Methylenedi-p-phenyl diisocyanate (260 effective MW) | 28.28 g |
| 6. | Dibutyl tin dilaurate | 0.2 g |
| 7. | Ethanol | 5.0 g |
| 8. | 1.0 N. Sodium Hydroxide | 37.5 mL |
| 9. | Deionized water | as needed to bring reagent 8 to 225 g |

The emulsion was prepared following the procedure outlined in the synthesis of polyurethane C. The yield was 277.5 g (46.7% solids). The neutralization equivalent of the emulsion was 0.084 meq/g. This corresponds to a neutralization equivalent of 0.180 meq/g on a 100% solids basis.

Polyurethane H.

A polyurethane with a composition similar to that of Polyurethane A was prepared to contain 16.7% by weight dimethylol propionic acid (total carboxylate functionality: 1.25 meq./g). The product was isolated as an emulsion in water.

Reagents:

| 1a. | Polypropylene glycol (1000 molecular weight) | 34.15 g |
| 1b. | Polypropylene glycol (3000 molecular weight) | 47.39 g |
| 2. | Polyethylene glycol (8000 molecular weight) | 10.01 g |
| 3. | Dimethylol propionic acid | 33.43 g |
| 4. | 2-Butanone | 200.08 g |
| 5. | Methylenedi-p-phenyl diisocyanate (257 effective MW) | 75.19 g |
| 6. | Dibutyl tin dilaurate | 0.20 g |
| 7. | Ethanol | 5.02 g |
| 8. | 0.926 N sodium hydroxide | 108 mL |
| 9. | Deionized water | as needed to bring reagent 8 to 325 g |

The emulsion was prepared following the procedure outlined for the preparation of polyurethane C. The isolated yield was 510 g (35.9% solids). The neutralization equivalent of the emulsion was 0.25 meq/g. This corresponds to a neutralization equivalent of 0.71 meq/g on a 100% solids basis.

Polyurethane J.

A polyurethane was prepared according to the specifications of JP 47-46332, Actual Example 2, for the purpose of comparison. This polyurethane was reported to be useful as a hair fixative in predominantly aqueous formulations.

In this example, triol with 500 molecular weight was used in an amount adjusted relative to the other reagents in order to match the hydroxyl to isocyanate molar ratio of JP 47-46332 Actual Example 2.

Reagents:

| 1. | TPEG 500 (polyoxyethylene glycerol triol with average molecular weight of 500 available from Union Carbide) | 277.80 g |
| 2. | Hylene W (methylene bis-(4-cyclohexyl isocyanate) (from DuPont) | 16.69 g |
| 3. | TDI-80 (effective molecular weight 182) | 16.71 g |
| 4. | Polyethylene glycol (200 molecular weight) | 8.39 g |
| 5. | Ethanol | 316.8 g |

A one liter four-neck round bottom flask was equipped with a mechanical stirrer, thermometer, a gas inlet-topped condenser, and a 125 mL pressure equalized addition funnel. The reaction vessel was placed under a positive pressure of nitrogen and was maintained in this manner throughout the course of the urethane condensation reaction. The vessel was charged with reagent 1, and the reaction was warmed to 60° C. using an oil bath. Reagents 2 and 3 were charged into the addition funnel. The mixture in the addition funnel was added drop-wise to the reaction over 20 minutes. The reaction was held at 60° C. for 3 hr. after the addition was complete.

At this point, reagent 4 was added in one portion, and the temperature of the reaction was raised to 120° C. The reaction was held at 120° C. for 1 hr.

The reaction was then cooled to <80° C. and reagent 5 was added. A homogenous solution was obtained with a concentration of about 50% solids.

Polyurethane K.

A polyurethane containing 11.9% dimethyl propionic acid (total carboxylate functionality: 0.89 meq/g) was prepared according to the specifications of U.S. Pat. No. 3,412,054, Actual Example 7, for the purpose of comparison. The process of that Example 7 was modified by substitution of organic solvents 1,4-dioxane, n-propoxypropanol, and n-butyl ether of diethylene glycol with methylethyl ketone, which is more readily removed from the final product. The process modification should not affect the properties of the resin.

Reagents:

| 1. | Polypropylene glycol (Mn 425) | 68.95 g |
| 2. | 1,4-Cyclohexanedimethanol | 23.81 g |
| 3. | Dimethylol propionic acid | 23.81 g |
| 4. | 2-Butanone | 315.00 g |
| 5. | Toluene diisocyanate | 83.49 g |
| 6. | Dibutyl tin dilaurate | 0.20 g |
| 7. | Ethanol | 6.1 g |
| 8. | N,N-Dimethylethanolamine | 6.65 g |
| 9. | Deionized water as needed to bring reagent 8 to 450 g | |
| 10. | N,N-Dimethylethanolamine | 8.09 g |

The emulsion was prepared following the procedure outlined for the preparation of polyurethane C with the following exception: reagent 10 was added portion-wise to the reaction mixture while the solvent was distilled from the reaction mixture. The isolated yield was 648.5 g (31.8% solids). The polymer was found to be fully neutralized; the pH of the emulsion was 8.97.

Polyurethane L.

A polyurethane was prepared containing 5.2% by weight dimethylol propionic acid (total carboxylate functionality: 0.39 meq/g). The product was obtained as an emulsion in water.

Reagents:

| | | |
|---|---|---|
| 1. | Polypropylene glycol (2025 molecular weight) | 150.0 g |
| 2. | Dimethylol propionic acid | 12.0 g |
| 3. | Isophorone diisocyanate | 66.6 g |
| 4. | Triethylamine | 9.3 g |
| 5. | Deionized water | 461.0 g |

A one liter four-neck round bottom flask was equipped with a mechanical stirrer, thermometer, stopper and a gas inlet-topped condenser. The reaction vessel was charged with reagents 1 and 2, and then heated to 120° C. for 30 minutes with a strong nitrogen purge to drive away any moisture. The mixture was then cooled to 80° C. Reagent 3 as added, and the reaction was held at 80° C. for 3 hours. The mixture was cooled to 60° C., and reagent 4 was added slowly over a period of 15 minutes. The reaction mixture was thoroughly agitated for 10 minutes. Reagent 5 at room temperature was then added rapidly to the reactor. The reaction mixture became dispersed in water after a few minutes.

The characteristics of the final dispersion were: solids 33.8%; pH 6.85; viscosity<50 cP; and particle size 76 nm.

Hair Fixative Formulations

Each of the prepared polyurethane emulsions was formulated into an aerosol hair spray and compared to a control as follows. Each of the emulsions was initially diluted with water to a manageable viscosity and then neutralized with 2-amino-2-methyl-1-propanol (AMP) to bring the polyurethane into solution or dispersion. The percentage neutralization was determined on the basis of the carboxylic acid monomer content of the polymer and was generally about 50-90% of the free acidity. The solution was then further diluted to 4 parts active polymer solids by the addition of dimethyl ether, or a blend of ethanol and ether. Formulations were made at 4 parts solids to attain equivalence with the percentage of polymer used in the control hair spray formulation. The polymer used in the control hair fixative formulation was a commercially available octyl-acrylamide/acrylates/t-butylaminoethylmethacrylate copolymer. The formulations were tested for curl retention against the control according to the procedure described after the tables of results. The values for the curl retention test are given as percentages. A Seaquist NS-34 valve (0.013" stem, 0.013" vapor tap, 0.040" dip tube, and 0.016" actuator) was used for spraying.

Polyurethane A exemplified the characteristics desired for hair fixative formulations. It formed clear films upon draw down, had a relatively misty spray pattern, and was soluble in low VOC systems. Therefore, it was formulated into 33% and 55% VOC systems (VOC percentage based on the total weight of the composition) as shown in Table 1 and tested for high humidity curl retention. The results are set out in Table 2 and show that polyurethane A performed better than the control in both the 33% and 55% VOC systems.

TABLE 1

| | Aerosol Formulations in Weight Percent | | | |
|---|---|---|---|---|
| VOC Formula | 33% VOC | 33% VOC | 55% VOC | 55% VOC |
| Polyurethane A | 10.65* | — | 10.65* | — |
| Control polymer | — | 4.00 | — | 4.00 |
| AMP | 00.24 | 00.79 | 00.24 | 00.79 |
| Ethanol | 00.00 | 00.00 | 22.00 | 22.00 |
| Water | 56.11 | 62.21 | 34.11 | 40.21 |
| DME | 33.00 | 33.00 | 33.00 | 33.00 |
| Total | 100.00 | 100.00 | 100.00 | 100.00 |

*corresponds to 4 parts active polymer

TABLE 2

| | High Humidity Curl Retention at 90% RH, 21° C. | | | | | | | | |
|---|---|---|---|---|---|---|---|---|---|
| | 15 min | 30 min | 60 min | 90 min | 2 hrs | 3 hrs | 4 hrs | 5 hrs | 24 hrs |
| 33% VOC | | | | | | | | | |
| A | 97.51+ | 95.00+ | 93.78+ | 91.27+ | 91.27+ | 91.27+ | 89.99+ | 89.99+ | 89.33+ |
| Control | 93.12 | 89.92 | 86.8 | 84.27 | 82.36 | 82.36 | 81.73 | 81.73 | 81.73 |
| 55% VOC | | | | | | | | | |
| A | 94.03+ | 91.42+ | 87.37+ | 84.75+ | 82.10+ | 78.78+ | 76.21 | 76.21 | 75.55 |
| Control | 89.67 | 84.08 | 80.67 | 77.80 | 75.84 | 73.04 | 71.69 | 71.69 | 70.99 |

+indicates sample is superior to control at a 95% confidence level
−indicates sample is inferior to control at a 95% confidence level otherwise there is no significant difference at a 95% confidence level The polyurethane A 33% VOC system was also compared to the control for the characteristics of stiffness, resistance to combing, flake accumulation, gloss, static, length of time of initial tackiness, drying time, and removability. The polyurethane system was superior to the control in stiffness and resistance to combing at a 95% confidence level, and comparable to the control on the other characteristics.

The spray characteristics were also compared and polyurethane A showed reduced foaming in both the 55% and 33% VOC systems compared to the control. As was previously noted, many polymers developed for the current high VOC sprays increase in viscosity when used in aqueous ethanol systems. The viscosity is especially pronounced at higher solids. At 10% solids in water, with a #21 spindle, at 50 rpm and 25° C., polyurethane A had a viscosity of 13–16 mPa.s and the control had a viscosity of 109 mPa.s. The lower viscosity of the polyurethane is a contributing factor to the reduced foaming observed in the formulated 55% and 33% VOC systems.

Based on these results, the remaining polyurethanes B through G were formulated into 33% VOC aerosol systems and tested for curl retention. Polyurethane B contained 2% by weight of N-methyl diethanol amine and 14.6% by weight of dimethylol propionic acid (DMPA), making the polymer amphoteric. An aerosol formulation containing polyurethane B was neutralized to 60% and gave a clear solution that performed comparably to the control.

Polyurethane C contained 24.6% DMPA and had low viscosity. When formulated into an aerosol, it performed equivalent to the control in curl retention and subjective properties (stiffness, flake accumulation, combing resistance, gloss, and static dissipation). Polyurethane D contained 7.5% by weight DMPA and showed a decrease in properties relative to the control.

Polyurethane E contained 14.6% by weight of DMPA and was prepared from a cycloaliphatic diisocyanate. (Polyurethanes A–D were prepared from an aromatic diisocyanate.) Polyurethane E performed comparably to the control in curl retention.

Polyurethane F was prepared without any polyethylene glycol and when formulated into an aerosol, performed comparably to the control.

Polyurethane G was prepared with 5% by weight DMPA. After neutralization, it became an unstable opaque solution, and when formulated with dimethyl ether in an attempt to make an aerosol system, the system still contained excessive precipitate. Attempts to formulate polyurethane G into a 55% VOC system were also unsuccessful.

The formulations and performance results are set out in the following tables.

TABLE 3

| Polyurethane | Aerosol Formulations in Weight Percent | | | | | | |
|---|---|---|---|---|---|---|---|
| | B | C | D | E | F | G | Control** |
| Polymer | 10.65* | 11.73* | 16.74* | 12.86* | 10.90* | 8.57* | 4.00* |
| AMP | 00.12 | 00.24 | 00.10 | 00.24 | 00.24 | 00.04 | 00.79 |
| Water | 56.23 | 55.03 | 50.16 | 53.90 | 55.86 | 58.39 | 62.21 |
| DME | 33.00 | 33.00 | 33.00 | 33.00 | 33.00 | 33.00 | 33.00 |
| Total | 100.00 | 100.00 | 100.00 | 100.00 | 100.00 | 100.00 | 100.00 |

*corresponds to 4 parts active polymer
**commercially available Octylacrylamide/Acrylates/t-butylaminoethylemethacrylate Copolymer

TABLE 4

| | High Humidity Curl Retention at 90% RH, 21° C. | | | | | | | | |
|---|---|---|---|---|---|---|---|---|---|
| Polymer | 15 min | 30 min | 60 min | 90 min | 2 hrs | 3 hrs | 4 hrs | 5 hrs | 6 hrs |
| Control | 97.35 | 96.03 | 94.53 | 93.66 | 91.42 | 90.39 | 90.35 | 89.85 | 90.43 |
| B | 97.87 | 96.80 | 95.57 | 94.77 | 94.82 | 94.65 | 95.08 | 94.18 | 94.00 |
| C | 94.90 | 94.76 | 95.77 | 94.35 | 93.91 | 92.71 | 92.18 | 91.98 | 90.98 |

TABLE 5

| | High Humidity Curl Retention at 90% RH, 21° C. | | | | | | | | |
|---|---|---|---|---|---|---|---|---|---|
| Polymer | 15 min | 30 min | 60 min | 90 min | 2 hrs | 3 hrs | 4 hrs | 5 hrs | 24 hrs |
| Control | 89.86 | 87.69 | 84.07 | 84.35 | 84.48 | 82.10 | 82.29 | 80.31 | 78.55 |
| D | 90.55 | 87.49 | 81.98 | 80.60 | 78.19– | 76.68 | 74.39– | 71.92– | 45.72– |
| E | 94.19+ | 91.51 | 91.25+ | 87.12 | 86.12 | 86.76 | 85.89 | 85.59 | 80.51 |

+indicates sample is superior to control at a 95% confidence level
–indicates sample is inferior to control at a 95% confidence level otherwise there is no significant difference at a 95% confidence level.

TABLE 6

| | High Humidity Curl Retention at 90% RH, 21° C. | | | | | | | | |
|---|---|---|---|---|---|---|---|---|---|
| Polymer | 15 min | 30 min | 60 min | 90 min | 2 hrs | 3 hrs | 4 hrs | 5 hrs | 6 hrs |
| Control | 93.12 | 89.92 | 86.80 | 84.27 | 82.36 | 82.36 | 81.73 | 81.73 | 81.73 |
| F | 93.07 | 90.61 | 86.84 | 85.61 | 84.37 | 83.74 | 83.10 | 83.10 | 82.46 |

Polyurethane E showed good properties in an aerosol formulation, and therefore was chosen as an exemplary polymer for formulation into an nonaerosol system. It was formulated into a completely aqueous system and compared to the control polymer for curl retention. The formulation and the test results are set out in Tables 7 and 8 and show that polyurethane E performed better than the control in the 0% VOC nonaerosol system.

TABLE 7

Non-aerosol Formulations in Weight Percent

| Polyurethane | E | Control** |
|---|---|---|
| Polymer | 12.86* | 4.00 |
| AMP | 00.26 | 00.98 |
| Water | 86.88 | 95.02 |
|  | 100.00 | 100.00 |

*corresponds to 4 parts active polymer
**commercially available Octylacrylamide/Acrylates/t-Butylaminoethylmethacrylate Copolymer

TABLE 8

Curl Retention

| Polymer | 15 min | 30 min | 60 min | 90 min | 2 hr | 3 hr | 4 hr | 5 hr | 24 hr |
|---|---|---|---|---|---|---|---|---|---|
| E | 89.45+ | 83.41+ | 78.65+ | 78.00+ | 76.73+ | 76.73+ | 75.99+ | 75.99+ | 67.86+ |
| Control | 79.39 | 69.51 | 66.77 | 66.77 | 64.63 | 63.93 | 63.93 | 63.28 | 54.79 |

+indicates sample is superior to control at a 95% confidence level
−indicates sample is inferior to control at a 95% confidence level otherwise there is no significant difference at a 95% confidence level.

Polyurethane H was prepared with 16.7% by weight DMPA and used for direct comparison with polyurethane J for stiffness, and humidity control. The stiffness test and humidity control test procedures are given after the tables of results. Both polyurethanes were prepared with 4% polymer solids, 22% anhydrous ethanol, 33% dimethyl ether, and the balance in water by weight. Polyurethane H was neutralized 95% with AMP; polyurethane J was used as synthesized. Polyurethane J was statistically inferior to polyurethane H in stiffness and humidity resistance at all time intervals. The results of the stiffness test are set out in Table 9 and show that Polymer H was superior in stiffness to the control, and both the control and Polymer H were far stiffer than Polymer J. The results of the curl retention test are set out in Table 10 and show that Polymer H was superior in humidity resistance to the control, and both the control and Polymer H gave significantly greater humidity resistance than Polymer J.

TABLE 9

Taber Stiffness Screening Test

|  | Stiffness | Deposition (mg) | Spray Rate (g/sec) |
|---|---|---|---|
| Control | 192 | 36 | .39 |
| Polymer H | 208 | 34 | .36 |
| Polymer J | 139 | 32 | .48 |

TABLE 10

High Humidity (90%) Curl Retention (Mean % Retention Values)

| Sample | 15 min. | 30 min. | 60 min. | 90 min. | 2 hrs. | 3 hrs. | 4 hrs. | 5 hrs. | 24 hrs. |
|---|---|---|---|---|---|---|---|---|---|
| Control | 93.82 | 91.12 | 88.39 | 86.39 | 83.52 | 81.47 | 81.47 | 81.47 | 81.47 |
| Polymer H | 94.73 | 92.72 | 89.38 | 86.06 | 84.75 | 83.41 | 82.75 | 82.75 | 80.71 |
| Polymer J | 69.20 | 58.60 | 48.83 | 44.59 | 42.13 | 35.95 | 35.02 | 34.28 | 29.03 |

Polyurethane K was prepared with 11.9% by weight DMPA and used for direct comparison with polyurethane E. Polyurethane K was not compatible with dimethylether in a 55% VOC formulation, and precipitated out after one day. Polyurethane E became and remained a clear (yellow tint), stable solution. Polyurethanes K and E were also formulated into an 85% VOC (ethanol) hair spray and tested for removability, and tack and drying time. The test procedures are given below. In all three tests polyurethane K was inferior to E at a 95% confidence level.

Polyurethane L was prepared with 5.2% by weight DMPA to give 0.39 meq/g of carboxylate functionality. This polymer formed a stable opaque dispersion in dimethyl ether at 55% VOC. It was formulated into an alcohol free hair spray and compared to the control polymer in an anhydrous formulation (both at 5 parts active polymer) for stiffness and curl retention. The formulation and results are set out in Tables 11–13.

TABLE 11

| | Aerosol Formulations in Weight Percent | | |
|---|---|---|---|
| Polyurethane | L | Control** 1 | Control** 2 |
| Polymer | 15.29* | 5.00 | 5.00 |
| AMP | — | 00.82 | 0.82 |
| Water | 51.71 | 61.18 | — |
| A-46 propellant*** | — | — | 25.00 |
| DME | 33.00 | 33.00 | — |
| Ethanol | — | — | 69.18 |
| Total | 100.00 | 100.00 | 100.00 |

*corresponds to 5 parts active polymer
**commercially available Octylacrylamide/Acrylates/t-butylaminoethyl-methacrylate Copolymer
***80% isobutane/20% propane

TABLE 12

| | Stiffness | | |
|---|---|---|---|
| Sample | Stiffness | Deposition (mg) | % of Control |
| Control #2, anhydrous | 320 | 61 | — |
| Polyurethane L | 249 | 51 | 78 |

The results show that the alcohol free formulation containing polyurethane L approached the performance characteristics of the commercial anhydrous formulation.

TABLE 13

| | High Humidity Curl Retention at 90% RH, 21° C. | | | | | | | | |
|---|---|---|---|---|---|---|---|---|---|
| Polymer | 15 min | 30 min | 60 min | 90 min | 2 hr | 3 hr | 4 hr | 5 hr | 24 hr |
| Control #1 | 89.86 | 87.69 | 84.07 | 84.35 | 84.48 | 82.10 | 82.29 | 80.31 | 78.55 |
| L | 100.00 | 97.24 | 95.93 | 94.59 | 94.59 | 93.93 | 89.12 | 82.66 | 75.87 |

The results show that the alcohol free formulation containing polyurethane L approached the performance characteristics of the commercial polymer in an alcohol-free system.

Curl Retention Test Procedure

Each of the hair spray formulations prepared from polymers A to G was tested on nine swatches of strands of Remi Blue String European Brown hair for curl retention at 90% relative humidity, 22° C. (72° F.), and the results pooled and averaged. The hair spray formulations for polymers H and J were tested on three 4¼" swatches of brown European virgin hair and the results pooled and averaged.

The testing procedure was as follows: The hair was separated into swatches of approximately 2 grams in weight and bound at one end with cotton thread and epoxy glue. Each swatch was then washed in a 10% solution of shampoo, and rinsed in warm tap water. The hair was cut into 6 inch lengths from the secured end and dried at 49° C. (120° F.). It was wet again and combed, and the excess water squeezed out. The hair swatch was then rolled and secured onto a ½ inch diameter Teflon® mandrel, and dried at 49° C. (120° F.). When dried, it was removed from the mandrel and the resulting curl suspended by its bound end. For each swatch, the curl height was measured, and then the curl was sprayed uniformly with four sprays per side of nonaerosol formulation, or for two seconds per side with aerosol formulation. The curl was laid on a horizontal surface and allowed to air dry for one hour. The dried curl was then resuspended and set into a chamber at 22° C. (72° F.), 90% relative humidity, and the curl height measured immediately, and at 15, 30, 60 minute, and 2, 3, 4, 5, 6 and 24 hour intervals.

The percentage curl retention was calculated by the formula $(L-L^r)/(L-L^\circ) \times 100$, where L is the length of hair fully extended, $L^\circ$ is the length of hair before spray and exposure, and $L^r$ is the length of hair after spray and exposure.

Taber Stiffness Test Procedure

Hair spray formulations from polymers H and J were tested for stiffness on three 4¼" swatches of brown European virgin hair and the results pooled and averaged. The swatches were first dried in an oven at 110° F. for 30 minutes to remove moisture and then dried in a desiccator for 15 minutes. The swatches were weighed and the weight recorded as $W_1$. Each swatch was sprayed with a hair spray formulation for one second and then clipped to a retention board and dried in a 110° F. oven for 15 minutes. The swatches were cooled in the desiccator and reweighed. This weight was recorded as $W_2$. The swatches were then placed to equilibrate overnight at 50% relative humidity and 23° C.

Stiffness was tested using a Taber V-5 Stiffness Tester from Taber Industries of North Tonawanda, N.Y., designed for evaluating stiffness and resilience of paper, cardboard and other flexible materials. The following procedure and calculation were adapted for use with hair samples.

When the machine is first turned on, the optical encoder inside the unit must be oriented before use. To do this, rotate the driving disc left and right beyond the zero, using the control lever switch; then return to zero.

Next, balance the pendulum by adjusting the levelers at the bottom of the two front legs until the line on the pendulum is directly under the zero line on the 100 graduation scale. Slide the 500 unit weight over the stud on the bottom of the pendulum. This weight multiplies each dial indication by five times.

Insert the swatch between the clamp jaws, with the lower edge resting lightly on the bottom gauge. Tighten the clamp jaws by turning the screws on either side of the clamp.

To center the swatch between the bottom rollers, use the left screw to move the left hand roller until it makes contact with the swatch, but does not deflect the pendulum from zero. Then bring the right hand roller into light contact with the swatch by using the right roller screw.

With one finger, apply light pressure to the control lever switch and deflect the driving disc to the left until the line on the pendulum is under the 15° deflection mark. Releasing the control lever will act as a brake and stop the driving disc. Be sure to deflect the sample in a smooth, continuous motion without abrupt starts and stops.

Record the stiffness reading on the outer scale that falls opposite to the zero line on the driving disc (LS). Now deflect the same swatch to the right by 15° and take that stiffness reading (RS). Average the left and right readings and multiply by five. The product is the stiffness value for that swatch.

Removability Test Procedure

Spray eight hair swatches with experimental formulation and eight with control formulation and allow to dry at ambient conditions for 1 hour. For each swatch, rinse under tap water for 1 minute while working fingers into hair. Put wet swatches in 110° F. oven until dry. Pair off experimental swatches vs. control swatches, and evaluate subjectively for residual stiffness, flake, and feel properties. Analyze data for statistical differences at 95% confidence level.

Tack and Drying Time Test Procedure

Suspend eight sets of two untreated hair swatches, each separately. Spray one swatch of each set with experimental formulation and other swatch with control formulation simultaneously. Immediately feel swatches for tack and drying times. Record time that tack starts, tack ends, and when each swatch feels dry. Subtract tack start time from tack end time to obtain total tack time. The shorter tack and dry times, the better. Analyze results for statistical differences at 95% confidence level.

Those skilled in the art will recognize, or be able to ascertain using no more than routine experimentation, many equivalents to the specific embodiments of the invention described specifically above. Such equivalents are intended to be encompassed in the scope of the following claims.

We claim:

1. An aqueous based hair fixative composition that comprises
   (A) an effective percent by weight, based on the total weight of the hair fixative composition, of a fully reacted carboxylated linear polyurethane prepared from
      (i) one or more 2,2-hydroxymethyl-substituted carboxylic acids, represented by the formula

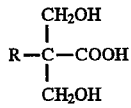

in which R represents $C_1-C_8$ alkyl, present in a sufficient amount by weight to give 0.35–2.25 milliequivalents of carboxyl functionality per gram of polyurethane,
      (ii) 10–90% by weight, based on the weight of the polyurethane, of one or more organic compounds, having a number average molecular weight of greater than 1000, selected from the group consisting of polyethylene glycol and polypropylene glycol, and
      (iii) one or more organic diisocyanates selected from the group consisting of methylene-di-p-phenyl diisocyanate, methylene-bis-(4-cyclohexylisocyanate), isophorone diisocyanate, and toluene diisocyanate and present in a sufficient amount to react with the active hydrogens of the 2,2-hydroxymethyl-substituted carboxylic acid and the organic compounds, excepting the hydrogen on the carboxylate of the 2,2-hydroxymethyl-substituted carboxylic acid;
   (B) an effective amount of one or more cosmetically acceptable organic or inorganic bases, selected from the group consisting of sodium hydroxide, potassium hydroxide, 2-amino-2-methyl-1-propanol, histidine, tris(hydroxymethyl)-aminomethane, triethanolamine, and triethylamine, to neutralize a sufficient proportion of the available carboxyl groups on the polyurethane to make the polyurethane soluble or dispersible in water or in a mixture of water and polar organic solvent; and
   (C) a solvent comprising
      (i) water, and
      (ii) 0–90%, by weight of the solvent, of one or more polar organic solvents selected from the group consisting of ethanol, propanol, isopropanol, butanol, dimethyl ether, acetone, methylethyl ketone and dimethoxymethane.

2. The hair fixative composition according to claim 1 in which the polyurethane is present in an amount from about 1–20% by weight of the hair fixative composition.

3. The hair fixative composition according to claim 1 in which the 2,2-hydroxymethyl-substituted carboxylic acid is present in an amount to give 0.5–1.85 milliequivalents per gram of polyurethane.

4. The hair fixative composition according to claim 1 in which the 2,2-hydroxymethyl-substituted carboxylic acid is 2,2-di-(hydroxymethyl)propionic acid.

5. The hair fixative composition according to claim 1 in which the organic compounds containing two active hydrogen atoms are present in an amount of 15–70% by weight of the polyurethane.

6. The hair fixative composition according to claim 1 in which the polyurethane is additionally prepared from a minor amount of organic compounds containing two active hydrogen atoms and having a number average molecular weight of less than 1000, the amount being insufficient to prevent solubility or dispersibility of the polyurethane in water.

7. The hair fixative composition according to claim 1 in which the amount of base for neutralization is sufficient to neutralize 50–100% of the total acidity of the polymer.

8. The hair fixative composition according to claim 1 in which the polar solvent is present in an amount up to 80% by weight of the total hair fixative composition.

9. The hair fixative composition according to claim 1 in which the polar solvent is present in an amount up to 55% by weight of the total hair fixative composition.

10. The hair fixative composition according to claim 1 in which the polar solvent is present in an amount up to 20% by weight of the total hair fixative composition.

11. The hair fixative composition according to claim 1 which further comprises up to 60% by weight of a propellant based on the weight of the total hair fixative composition.

12. The hair fixative composition according to claim 11 in which the propellant is selected from the group consisting of dimethyl ether, $C_3-C_6$ straight and branched chain hydrocarbons, hydrofluorocarbons, and compressed gases.

* * * * *